US010773035B2

(12) United States Patent
Klinger et al.

(10) Patent No.: US 10,773,035 B2
(45) Date of Patent: Sep. 15, 2020

(54) CPAP MACHINE STORAGE STAND

(71) Applicants: Darin Klinger, Harrisburg, PA (US); Jack Gross, Jr., Windfield, PA (US)

(72) Inventors: Darin Klinger, Harrisburg, PA (US); Jack Gross, Jr., Windfield, PA (US)

(*) Notice: Subject to any disclaimer, the term of this patent is extended or adjusted under 35 U.S.C. 154(b) by 294 days.

(21) Appl. No.: 15/787,039

(22) Filed: Oct. 18, 2017

(65) Prior Publication Data
US 2018/0272086 A1 Sep. 27, 2018

Related U.S. Application Data

(60) Provisional application No. 62/474,318, filed on Mar. 21, 2017.

(51) Int. Cl.
*A61M 16/00* (2006.01)
*A61G 7/05* (2006.01)
(Continued)

(52) U.S. Cl.
CPC ....... *A61M 16/0003* (2014.02); *A61B 5/4818* (2013.01); *A61F 5/56* (2013.01);
(Continued)

(58) Field of Classification Search
CPC .......... A61M 16/0003; A61M 16/0497; A61M 16/06; A61M 2209/08; A61M 2209/082; A61M 2209/084; A61M 2209/086; A61M 16/0875; A61M 16/0683; A61G 7/0503; A61G 12/00–008; F16L 3/00; F16L 3/003; D06F 57/06; D06F 57/08; D06F 75/20; D06F 75/34; D06F 75/40; D06F 79/00; D06F 79/02; A47B 3/00; A47B 3/002; A47B 3/08; A47B 2003/025; A47B 3/0803; A47B 13/08; A47B 2003/0821; A47B 2003/0827; A47B 2013/022; A47B 23/00–001; A47B 23/002–004; A47B 23/02–025; A47G 25/0664; A47C 21/00–006; A47C 7/62
USPC ........... 5/503.1–507.1, 658–659; 108/42–49, 108/153.1, 156, 158; 211/41.1–41.9, 211/133.6, 119.006, 134, 144, 186, 149, 211/164; 248/125.8–125.9, 130, 131, 248/349.1, 424, 425, 441.1, 447, 458, 248/459, 460, 461
See application file for complete search history.

(56) References Cited

U.S. PATENT DOCUMENTS 7,744,043 B2    6/2010  Otinger
8,181,918 B2    5/2012  McCloud
(Continued)

*Primary Examiner* — Kendra D Carter
*Assistant Examiner* — Elliot S Ruddie
(74) *Attorney, Agent, or Firm* — Boudwin Intellectual Property; Daniel Boudwin

(57) ABSTRACT

A continuous positive airway pressure (CPAP) machine storage stand. The CPAP machine storage stand includes a base having a lip extending perpendicularly away from a periphery of the base defining an interior portion of the base. The interior portion can receive a CPAP machine therein. A U-shaped frame having a first end and a second end is hingedly affixed to opposing sides of the lip at the first and second ends thereof. The U-shaped frame can selectively move between a deployed position and a collapsed position, wherein the U-shaped frame rests flush against the base within the interior portion when in the collapsed position.

13 Claims, 6 Drawing Sheets

(51) Int. Cl.
*A61G 12/00* (2006.01)
*A61M 16/06* (2006.01)
*A61F 5/56* (2006.01)
*A61B 5/00* (2006.01)
*A61M 5/14* (2006.01)
*A61G 13/10* (2006.01)

(52) U.S. Cl.
CPC ......... *A61G 7/0503* (2013.01); *A61G 12/002* (2013.01); *A61M 5/1415* (2013.01); *A61M 16/06* (2013.01); *A61G 13/101* (2013.01); *A61G 13/107* (2013.01); *A61M 2209/082* (2013.01); *A61M 2209/084* (2013.01); *A61M 2209/086* (2013.01)

(56) References Cited

U.S. PATENT DOCUMENTS

| | | | |
|---|---|---|---|
| 8,534,618 B2 | 9/2013 | Mays | |
| 8,540,196 B1 * | 9/2013 | Hodson | F16L 3/012 248/121 |
| 9,060,599 B1 * | 6/2015 | Jones | A47B 23/025 |
| 9,609,943 B1 * | 4/2017 | Lin | A47C 4/14 |
| 2007/0181751 A1 * | 8/2007 | Newkirk | A61G 7/018 248/65 |
| 2008/0185359 A1 | 8/2008 | Baxter | |
| 2009/0039210 A1 | 2/2009 | Yates et al. | |
| 2009/0065005 A1 * | 3/2009 | Ades | A61M 16/06 128/205.25 |
| 2009/0107937 A1 * | 4/2009 | Watson, Sr. | A47B 23/02 211/133.6 |
| 2017/0197050 A1 * | 7/2017 | Reinburg | A61M 16/0497 |

* cited by examiner

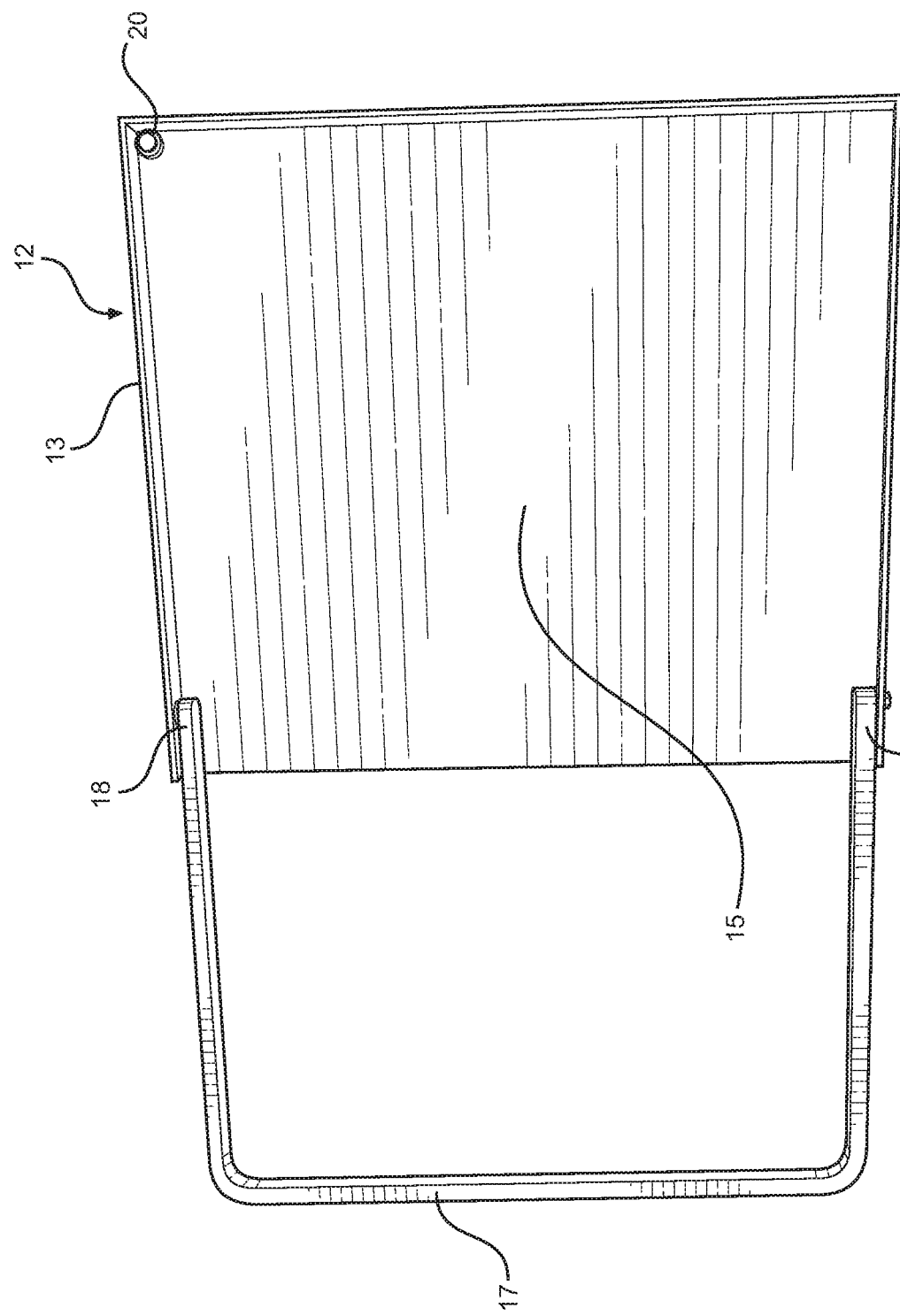

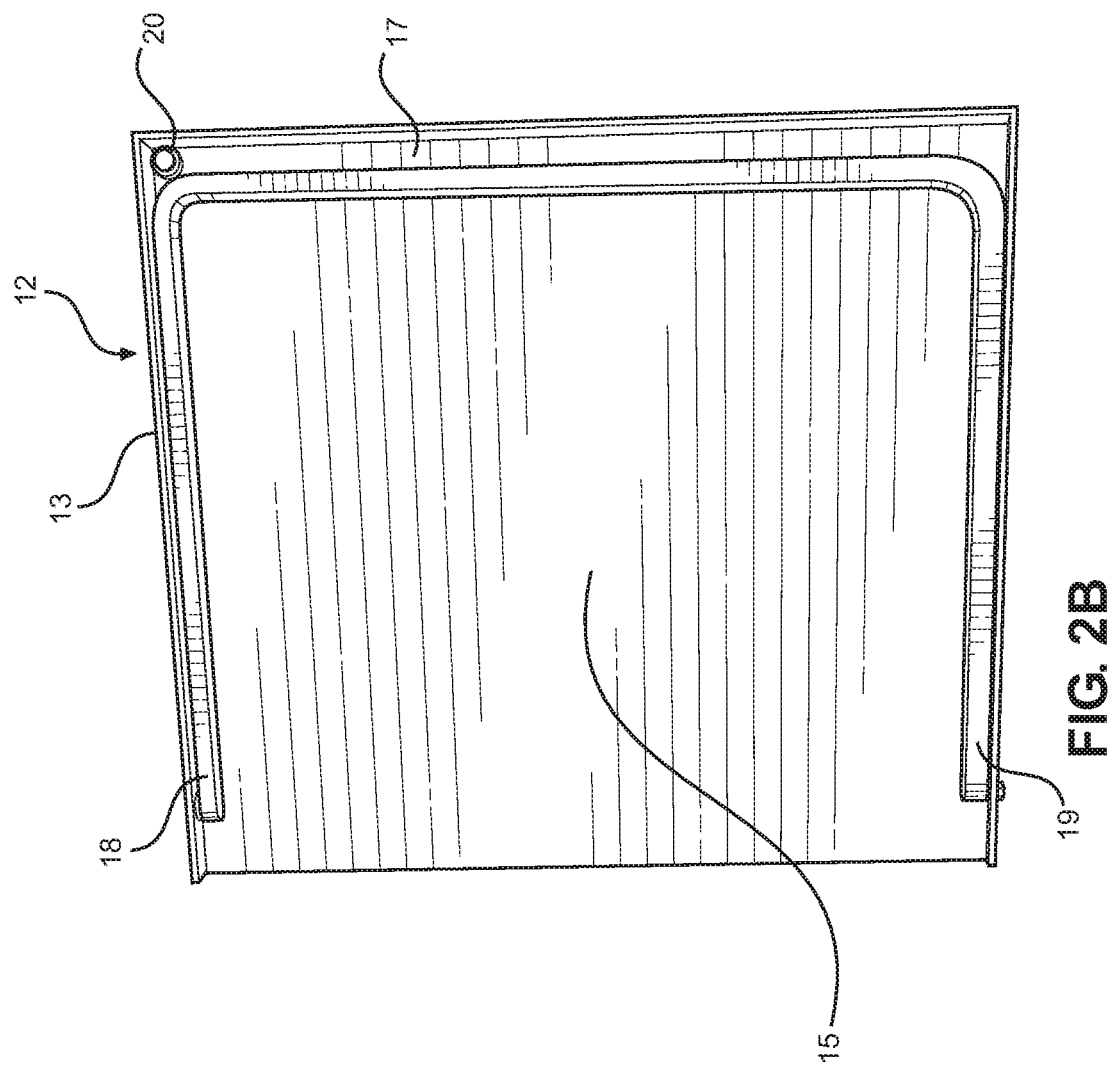

CPAP MACHINE STORAGE STAND

CROSS REFERENCE TO RELATED APPLICATIONS

This application claims the benefit of U.S. Provisional Application No. 62/474,318 filed on Mar. 21, 2017. The above identified patent application is herein incorporated by reference in its entirety to provide continuity of disclosure.

BACKGROUND OF THE INVENTION

The present invention relates to CPAP machine storage stands. Specifically, it relates to a CPAP machine storage stand having a collapsible U-shaped frame configured to removably secure the storage stand to a bed frame between a mattress and a box-spring.

Many people suffer from sleep apnea, a condition that causes periods of shallow breathing or pauses in breathing during sleep. This can disrupt normal sleep patterns, leading to sufferers experiencing fatigue and sleepiness throughout the day. Many people with sleep apnea use a continuous positive airway pressure (CPAP) machine to deliver a constant flow of air pressure to a user's airway, preventing the airway from collapsing or becoming blocked during sleep and allowing the user to sleep soundly. These CPAP machines, however, require daily maintenance for optimal and sanitary use. The CPAP machine includes a base unit, associated face masks, nasal pillows, tubes, and other accessories, which must all be kept clean and washed on a regular basis. Additionally, should any of these accessories fall onto a floor or other unsanitary surface, germs and undesirable microbes can accumulate thereon. Furthermore, CPAP machines and accessories tend to clutter other viable storage locations, such as a nightstand adjacent to a user's bed, thereby preventing the user from storing other objects on the nightstand. Therefore, a device that allows a user to store the CPAP machine and its associated accessories thereon, while also providing a sanitary place to store recently cleaned elements of the CPAP machine as they dry, is desired.

In light of the devices disclosed in the known art, it is submitted that the present invention substantially diverges in design elements from the known art and consequently it is clear that there is a need in the art for an improvement to existing CPAP machine storage stands. In this regard, the instant invention substantially fulfills these needs.

SUMMARY OF THE INVENTION

In view of the foregoing disadvantages inherent in the known types of CPAP machine storage stands now present in the prior art, the present invention provides a CPAP machine storage stand wherein the same can be utilized for providing convenience for the user when storing a CPAP machine adjacent to a bed for use during sleep.

The present system comprises a base having a lip extending perpendicularly away from a periphery of the base defining an interior portion of the base, wherein the interior portion is configured to receive a CPAP machine therein. A U-shaped frame having a first end and a second end is hingedly affixed to opposing sides of the lip at the first and second ends. The U-shaped frame is configured to selectively move between a deployed position and a collapsed position, wherein the U-shaped frame rests flush against the base within the interior portion when in the collapsed position. In some embodiments, an attachment point is disposed on the base opposite the first end. In another embodiment, the CPAP machine storage stand further comprises a plurality of arms, each having a lower end and an upper end, wherein the plurality of arms are configured to removably secure to each other at the upper and lower ends thereof. In other embodiments, the upper end comprises a threaded protrusion configured to engage with interior threading disposed within the lower end. In yet another embodiment, the plurality of arms includes an upper arm, wherein the upper end of the upper arm comprises a notch disposed about the circumference of the upper end. In some embodiments, the plurality of arms includes a lower arm, wherein the lower end of the lower arm is configured to removably secure to the attachment point. In another embodiment, the lower end of the lower arm comprises a greater cross-sectional area than the lower arm. In other embodiments, the CPAP machine storage stand further comprises a head removably securable to the upper end of the upper arm, such that a lower edge of the head engages the notch via friction fit. In yet another embodiment, the head further comprises an aperture therein, wherein the aperture is configured to receive a hose of the CPAP machine therethrough. In some embodiments, the head further comprises a pair of extensions extending from an upper side of the head at opposing sides thereof, wherein the pair of extensions form a recess therebetween. In another embodiment, the pair of extensions comprise an angled interior side.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 2A shows a perspective view of the base of an embodiment of the CPAP machine storage stand in the deployed position.

FIG. 2B shows a perspective view of the base of an embodiment of the CPAP machine storage stand in the collapsed position.

DETAILED DESCRIPTION OF THE INVENTION

Figure 1:
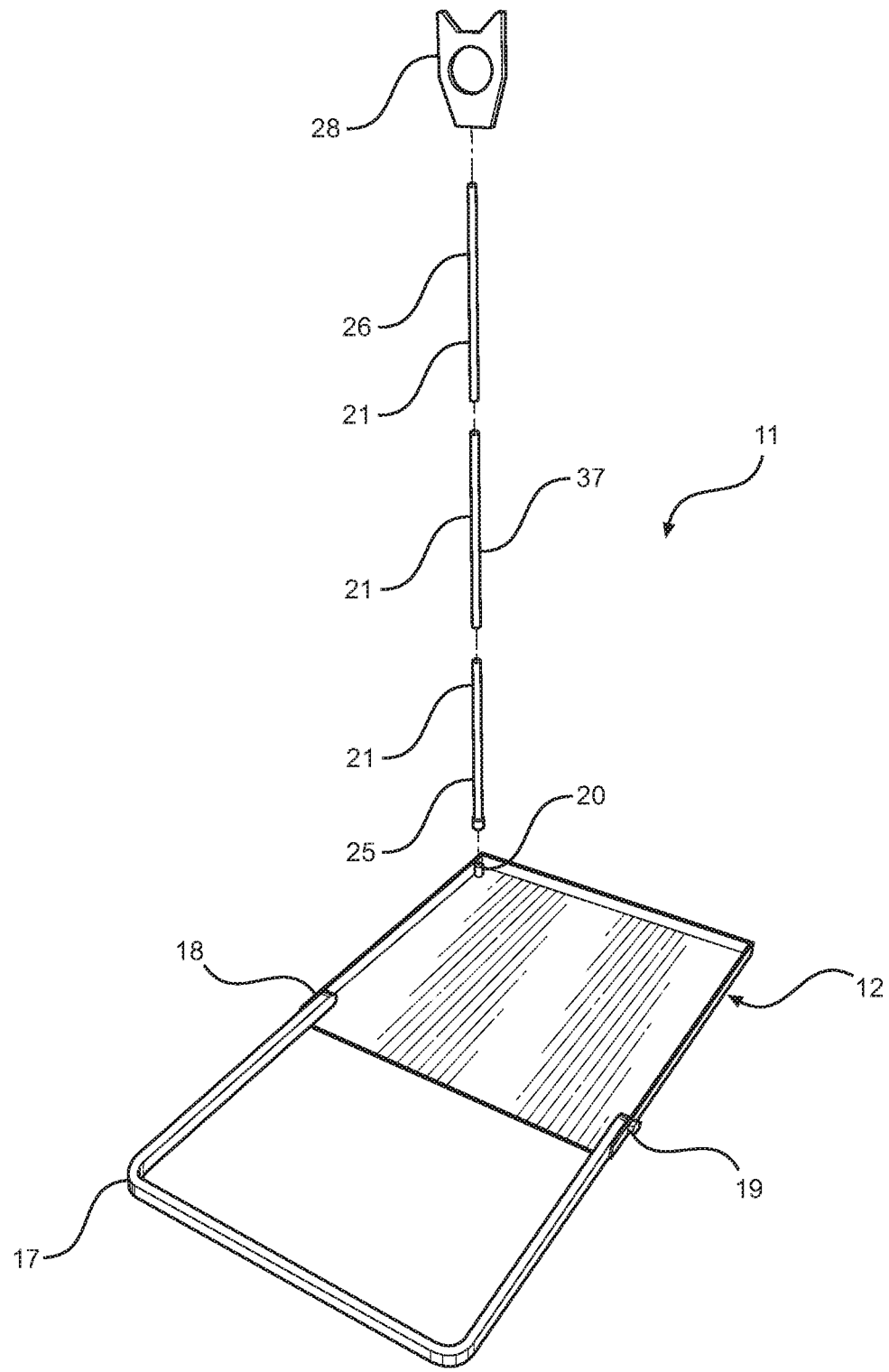
FIG. 1 shows an exploded view of an embodiment of the CPAP machine storage stand.

Reference is made herein to the attached drawings. Like reference numerals are used throughout the drawings to depict like or similar elements of the CPAP machine storage stand. The figures are intended for representative purposes only and should not be considered to be limiting in any respect.

Referring now to FIG. 1, there is shown an exploded view of an embodiment of the CPAP machine storage stand. The CPAP machine storage stand 11 comprises a base 12 having a U-shaped frame 17 hingedly affixed thereto at a first end 18 of the U-shaped frame 17 and a second end 19 of the U-shaped frame. The first and second ends 18, 19 are hingedly affixed to opposing sides of the base 12, such that the U-shaped frame 17 is configured to selectively move between a deployed position and a collapsed position so as to allow easier storage and transportation of the CPAP machine storage stand 11. In the illustrated embodiment, the base 12 further comprises an attachment point 20 disposed on the base 12 opposite the first end 18. A plurality of arms 21 are configured to removably secure to each other and the attachment point 20 such that an extended stand is formed. In some embodiments, the plurality of arms 21 removably secure to each other via friction fit, however, in alternate embodiments the plurality of arms 21 removably secure via a threaded connection. In the illustrated embodiment, the plurality of arms 21 comprises three arms 21, including an upper arm 26, a lower arm 25, and a middle arm 37 therebetween, wherein the lower arm 25 is removably secured to the attachment point 20. The middle arm 37 removably secures to the upper and lower arms 26, 25 thereby extending the length of the stand. A head 28 is removably secured to the upper arm 26, which in connection with the base 12, the lower arm 26, and the middle arm 37, forms the assembled CPAP machine storage stand 11.

Figure 5:
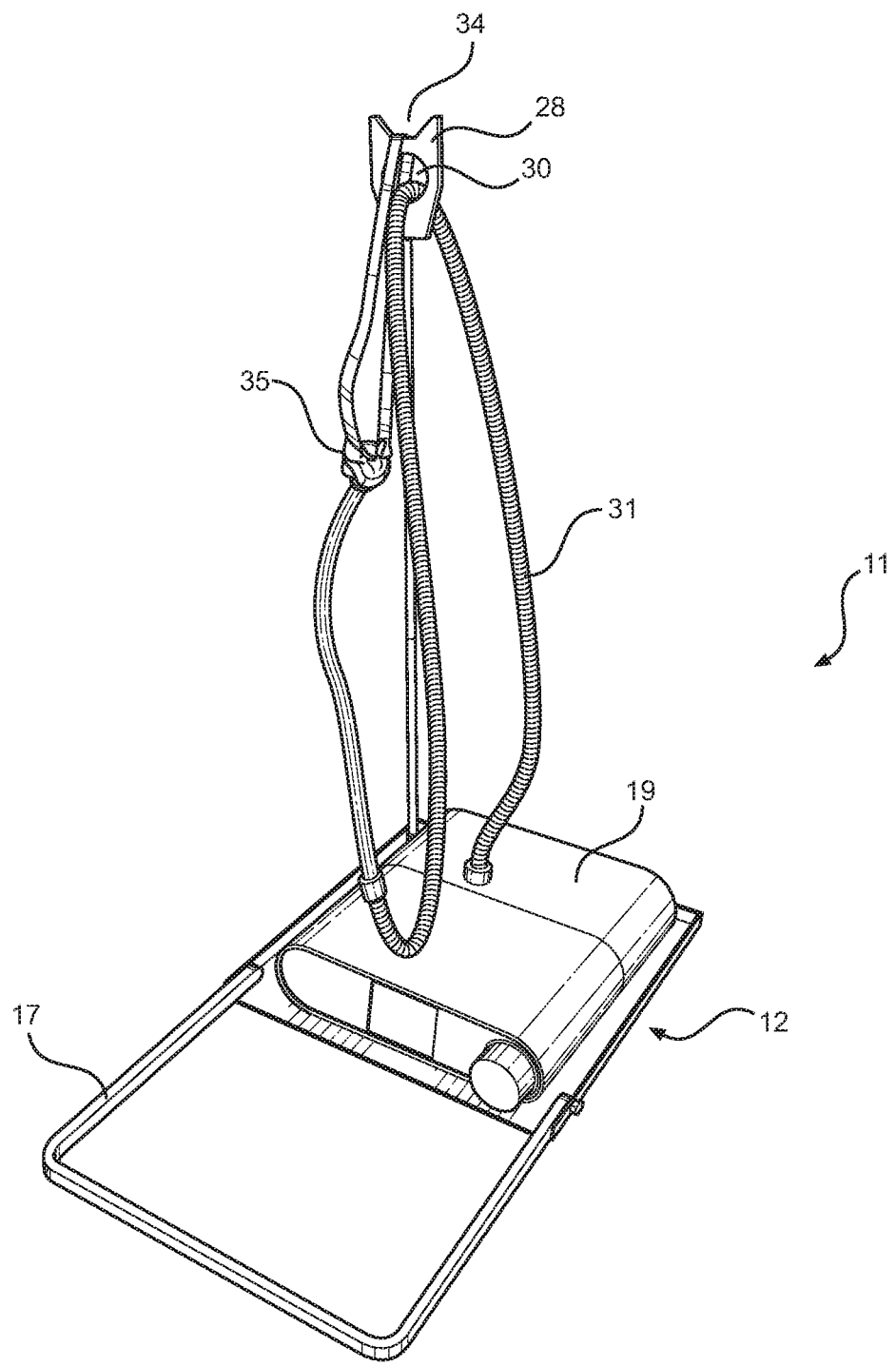
FIG. 5 shows a perspective view of an embodiment of the CPAP machine storage stand in use.

Referring now to FIGS. 2A and 2B, there is shown a perspective view of the base of an embodiment of the CPAP machine storage stand in the deployed position and a perspective view of the base of an embodiment of the CPAP machine storage stand in the collapsed position, respectively. In the illustrated embodiment, the base 12 comprises a lip 13 extending perpendicularly away from a periphery of the base 12. The lip 13 forms an interior portion 15 of the base 12, wherein the interior portion 15 is configured to receive a CPAP machine (as shown in FIG. 5, 16) therein. In the illustrated embodiment, the base 12 further comprises the attachment point 20, wherein the attachment point 20 is disposed opposite the first end 18. The attachment point 20 can be located anywhere along the periphery of the base 12, so as to provide enough surface area within the interior portion 15 to receive the CPAP machine. In the illustrated embodiment, the attachment point 20 comprises a threaded section so as to engage with threading within the lower arm.

The U-shaped frame 17 is hingedly affixed to the base 12 at the first and second ends 18, 19 of the U-shaped frame 17. In this way, the lip 13 prevents the CPAP machine from leaving the interior portion 15, while also providing a structure to which the first and second ends 18, 19 of the U-shaped frame 17 may be affixed. The U-shaped frame 17 is configured to selectively move between a deployed position and a collapsed position about the hinged connections at the first and second ends 18, 19. In the illustrated embodiment of FIG. 2A, the U-shaped frame 17 is shown in a deployed position, such that the U-shaped frame can be removably secured between a mattress and a box spring. In this way, the base 12 can extend outwards from the side of the user's bed, allowing the CPAP machine stored thereon to be conveniently located. The weight of the mattress provides a force on the U-shaped frame 17, such that the base can support the weight of the CPAP machine and associated accessories. In some embodiments, the U-shaped frame can be further secured to the bed frame or box spring via a fastener, such as a bracket. In the illustrated embodiment of FIG. 2B, the U-shaped frame is shown in the collapsed position, wherein the U-shaped frame 17 rests flush against a surface of the interior portion 15. In this way, the U-shaped frame 17 can be rotated to the collapsed position in order to reduce the amount of space the CPAP machine storage stand occupies, allowing a user to easily store and transport the CPAP machine storage stand.

Figure 3:
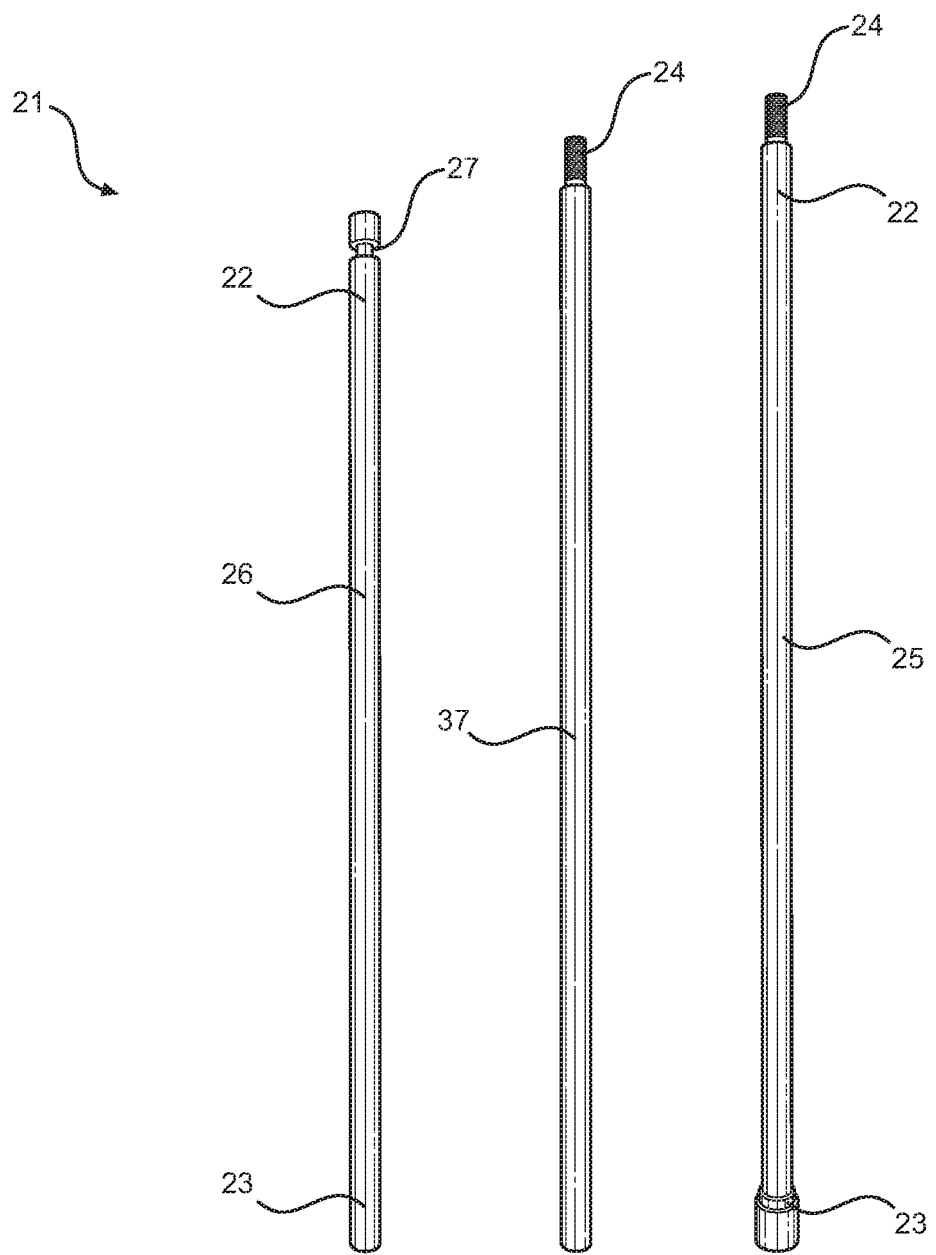
FIG. 3 shows a perspective view of the plurality of arms of an embodiment of the CPAP machine storage stand.

Referring now to FIG. 3, there is shown a perspective view of the plurality of arms of an embodiment of the CPAP machine storage stand. In the illustrated embodiment, the plurality of arms 21 comprise three arms, such that when disassembled, the plurality of arms 21 can occupy minimal space for easy storage and transportation. The remaining discussion will focus on the plurality of arms 21 comprising three arms, including a lower arm 25, an upper arm 26, and a middle arm 37. Fewer or additional arms are contemplated, wherein additional arms share the design of the middle arm 37. Each arm 21 comprises an upper end 22 and a lower end 23 wherein the upper end 22 of the lower arm 25 and the middle arm 37 comprises a threaded protrusion 24. The threaded protrusion 24 is configured to engage with internal threads disposed within the lower ends 23 of the plurality of arms 21, such that the upper end 22 of the lower arm 25 is removably secured to the lower end 23 of the middle arm 37, and the upper end 22 of the middle arm 37 is removably secured to the lower end 23 of the upper arm 26, creating an assembled stand. The lower end 23 of the lower arm 25 comprises internal threading configured to engage with the external threading disposed on the attachment point on the base. Additionally, in the illustrated embodiment, the lower end 23 comprises a larger cross-sectional area than the remainder of the lower arm 25, such that the increased area provides increased stability to the assembled plurality of arms 21. The upper end 22 of the upper arm 26 comprises a notch 27 disposed about the circumference of the upper end 22 of the upper arm 26. The notch 27 is configured to removably secure the head thereto.

Figure 4:
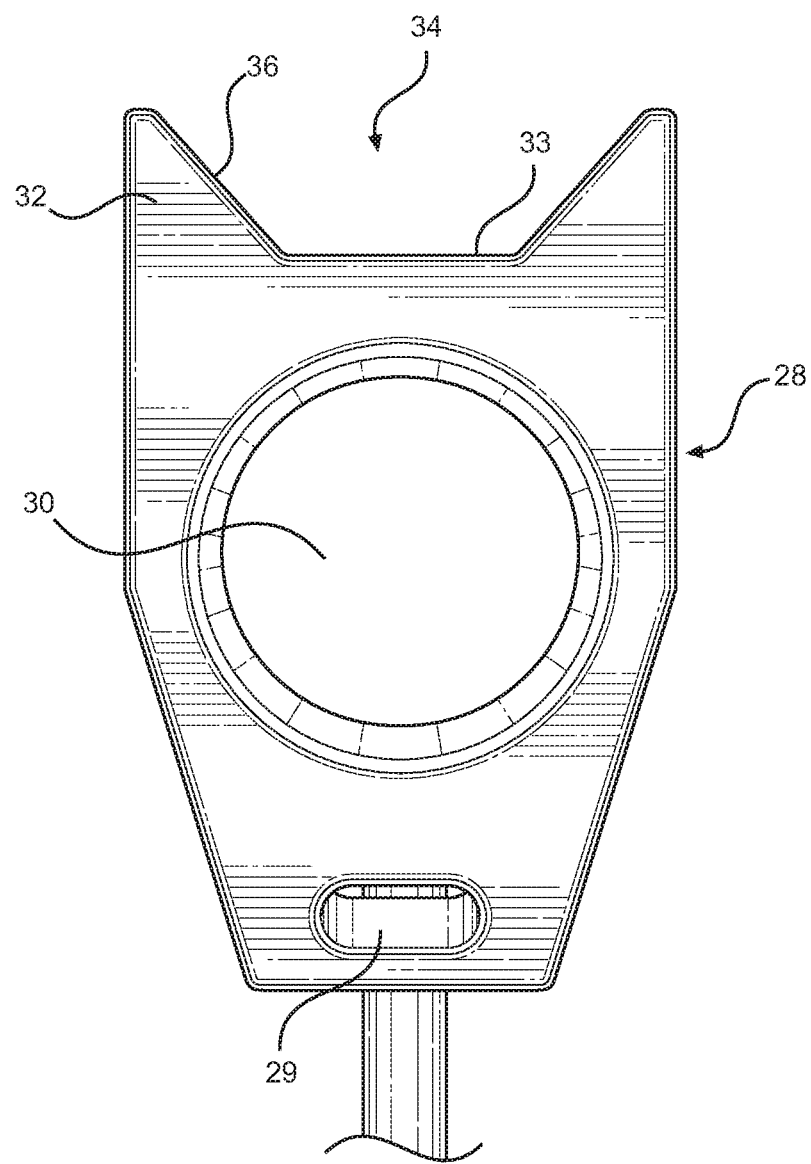
FIG. 4 shows a perspective view of the head of an embodiment of the CPAP machine storage stand.

Referring now to FIG. 4, there is shown a perspective view of the head of an embodiment of the CPAP machine storage stand. The CPAP machine storage stand further comprises a head 28 removably securable to the upper end of the upper arm. The head 28 comprises a lower edge 29, wherein the lower edge 29 engages with the notch of the upper arm via a friction fit, allowing the head 28 to securely affix thereto. In the illustrated embodiment, the head 28 further comprises an aperture 30, wherein the aperture 30 is configured to receive a hose (as shown in FIG. 5, 31) therethrough. In this way, the hose can be supported up and away from the CPAP machine, such that the user does not experience any pulling or other forces on the face of the user due to gravity acting on the hose when the CPAP machine is in use. Furthermore, the aperture 30 allows the hose to be hung therefrom, such that the hose can be extended for easier drying after cleaning.

In the illustrated embodiment, the head 28 further comprises a pair of extensions 32, wherein the pair of extensions 32 extend from an upper side 33 of the head 28, on opposing sides thereof. The pair of extensions 32 create a recess 34 therebetween, wherein the recess 34 is configured to receive a mask (as shown in FIG. 5, 35) of the CPAP machine therein. In this way, the recess 34 allows the mask to be within easy reach of the user when the user is resting in bed. Additionally, the recess 34 allows the user to hang the mask therein, such that the mask is kept away from unsanitary surfaces such as the floor, when the mask is not in use. In the illustrated embodiment, the pair of extensions 32 further comprise an angled inner side 36, wherein the angled inner side 36 provides a slope that allows a user to easily remove the mask from the recess 34, as the angled inner side 36 allows the mask to slide therealong. In this way, the user can avoid snagging the mask on the pair of extensions 32, preventing damage to the mask as well as eliminating frustration caused by struggling to remove the mask from the recess 34.

Referring now to FIG. 5, there is shown a perspective view of an embodiment of the CPAP machine storage stand in use. In one exemplary use, the user moves the U-shaped frame 17 to the deployed position, such that the user then places the U-shaped frame 17 under a mattress. In some embodiments, the user fastens the U-shaped frame 17 to the bed frame to further secure the CPAP machine storage stand 11 to the bed. When the U-shaped frame 17 is removably secured to the bed, the base 12 extends from the side of the bed. The user then places the CPAP machine 19 on the base. The plurality of arms are then assembled to create the assembled stand, and the user may then removably secure the head 28 to the upper end of the assembled arms. The user then feeds the hose 31 through the aperture 30, such that the hose 31 is suspended therefrom, and attaches the hose 31 to the mask 35. When the mask 35 is not in use, the mask 35 can be suspended from the head 28 via the recess 34, which prevents the mask 35 from contacting any unsanitary surfaces. As the user is lying in bed, the mask 35 can be removed from the recess 34 as the angled inner sides allow the user to slide the mask 35 out of the recess easily. After the user cleans the CPAP machine 19 and associated accessories, the CPAP machine storage stand 11 can be used to suspend the hose 31 and mask 35 therefrom, such that the CPAP machine 19, hose 31, and mask 35 are sufficiently ventilated to dry rapidly.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A CPAP machine storage stand, comprising:
   a base having a lip extending perpendicularly away from a periphery of the base defining an interior portion of the base;
   wherein the interior portion is configured to receive a CPAP machine therein;
   a U-shaped frame having a first end and a second end;
   wherein the first end and the second end are hingedly affixed to opposing sides of the lip;
   wherein the U-shaped frame is configured to move between a deployed position and a collapsed position;
   wherein an entirety of the U-shaped frame rests flush against a surface of the base within the interior portion when in the collapsed portion; and
   wherein the U-shaped frame is substantially parallel to the base when the U-shaped frame is in the deployed position.

2. The CPAP machine storage stand of claim 1, further comprising an attachment point disposed on the base opposite the first end.

3. The CPAP machine storage stand of claim 2, further comprising a plurality of arms, each arm having a lower end and an upper end, wherein the plurality of arms are configured to removably secure to each other at the upper and lower ends thereof.

4. The CPAP machine storage stand of claim 3, wherein the upper end comprises a threaded protrusion configured to engage with interior threading disposed within the lower end.

5. The CPAP machine storage stand of claim 3, wherein the plurality of arms includes a lower arm, wherein the lower end of the lower arm is configured to removably secure to the attachment point.

6. The CPAP machine storage stand of claim 5, wherein the lower end of the lower arm comprises a greater cross-sectional area than the upper end of the lower arm.

7. The CPAP machine storage stand of claim 3, wherein the plurality of arms includes an upper arm, wherein an upper end of the upper arm comprises a notch disposed about a circumference of the upper end.

8. The CPAP machine storage stand of claim 7, further comprising a head removably securable to the upper end of the upper arm, such that a lower edge of the head engages the notch via friction fit.

9. The CPAP machine storage stand of claim 8, wherein the head further comprises an aperture therein, the aperture configured to receive a hose of the CPAP machine therethrough.

10. The CPAP machine storage stand of claim 8, wherein the head further comprises a pair of extensions extending from an upper side of the head at opposing sides thereof, the pair of extensions forming a recess therebetween.

11. The CPAP machine storage stand of claim 10, wherein the pair of extensions comprise an angled inner side.

12. The CPAP machine storage stand of claim 1, wherein the lip extends from the periphery of the base along three contiguous sides thereof.

13. The CPAP machine storage stand of claim 9, wherein the head further comprises a pair of extensions extending from an upper side of the head at opposing sides thereof, the pair of extensions forming a recess therebetween.

\* \* \* \* \*